United States Patent [19]

Price et al.

[11] 4,066,744
[45] Jan. 3, 1978

[54] SEROLOGICAL REAGENT, TEST SLIDE AND METHOD FOR GONORRHEAL ANTIBODIES

[75] Inventors: Richard T. Price, Verona; Rita C. Prodell, West Orange, both of N.J.

[73] Assignee: Akzona Incorporated, Asheville, N.C.

[21] Appl. No.: 649,768

[22] Filed: Jan. 16, 1976

Related U.S. Application Data

[63] Continuation-in-part of Ser. No. 347,975, April 4, 1973, abandoned, which is a continuation-in-part of Ser. No. 214,213, Dec. 30, 1971, Pat. No. 3,770,383, which is a continuation-in-part of Ser. No. 131,172, April 5, 1971, Pat. No. 3,666,421, which is a continuation-in-part of Ser. No. 818,366, April 22, 1969, abandoned.

[51] Int. Cl.² .................. C12K 1/04; G01N 31/00; G01N 31/02; G01N 31/06
[52] U.S. Cl. .................... 424/12; 23/230 B; 23/253 TP; 424/11; 424/13; 424/78; 424/87; 424/92
[58] Field of Search ............ 424/3, 8, 11, 12, 13, 424/87, 92, 78; 230/230 B, 253 TP

[56] References Cited

U.S. PATENT DOCUMENTS

| | | | |
|---|---|---|---|
| 3,551,555 | 12/1970 | Schuurs | 424/12 |
| 3,770,383 | 11/1973 | Price | 424/12 X |
| 3,828,103 | 8/1974 | Fujita | 424/12 |

OTHER PUBLICATIONS

Reising, Applied Microbiology, vol. 21, May, 1971, pp. 852-853.
Cohen, J. of Bact., vol. 94, July 1967, p. 141-148.

*Primary Examiner*—Albert T. Meyers
*Assistant Examiner*—A. P. Fagelson
*Attorney, Agent, or Firm*—Robert H. Falk; Francis W. Young; Charles A. Wendel

[57] ABSTRACT

Disclosed are a reagent and test slide used for serological detection of gonorrheal antibodies in human blood serum or synovial fluid. The reagent comprises latex particles having absorbed on their surfaces an inert protein, such as bovine serum albumin and a heat labile antigen derived from Neisseria gonorrhoeae bacteria exhibiting $T_1$ colonial morphology. The reagent may be employed by several forms, for example, as a liquid suspension of the latex particles, or in the form of a dried deposit of the latex particles. Regardless of the form employed, the reagent is particularly useful as a routine screening test in hospitals and prenatal clinics to detect gonococcal infection in women and also in cases of complicated gonorrhea, e.g., gonorrheal arthritis where infection is not conveniently detectable by present means. The test slide may have dried thereon an absorbing antigen for heterophile antibodies. If desired, diagnosis made by the test of the invention can be subsequently confirmed by conventional more expensive and time consuming means, if this is thought to be desirable.

20 Claims, No Drawings

SEROLOGICAL REAGENT, TEST SLIDE AND METHOD FOR GONORRHEAL ANTIBODIES

CROSS-REFERENCE TO RELATED APPLICATIONS

This application is a continuation-in-part of application Ser. No. 347,975, filed Apr. 4, 1973 now abandoned, which is in turn a continuation-in-part of Ser. No. 214,213, filed Dec. 30, 1971 now U.S. Pat. No. 3,770,383 (issued Nov. 6, 1973), which is in turn a continuation-in-part of Ser. No. 131,172, filed Apr. 5, 1971, now U.S.. Pat. No. 3,666,421 (issued May 30, 1972), which is in turn a continuation-in-part of application Ser. No. 818,366, filed Apr. 22, 1969, now abandoned.

BACKGROUND OF THE INVENTION

Presently, the recognized test procedures for the determination of gonoccocal infection rely upon culture methods which are laborious, time-consuming, and in the case of asymptomatic infections present in females, the accuracy of cultural methods may be doubtful (see Pariser et al., Southern Medical Journal. Vol. 63, pages 198–201).

Typical procedures are described in the publication "Criteria and Techniques for the Diagnosis of Gonorrhea" published by the United States Public Health Service at the Venereal Disease branch in Atlanta, Georgia. Typically, in males, the presence of gonococcal infection is determined by obtaining urethral cultures which exhibit oxidase-portions colonies of gram-negative diplococci when cultured on Thayer-Martin medium (J. D. Thayer and J. E. Martin, Jr., in Public Health Rep., 79, pages 49–57). In females, gonococcal infection is diagnosed by cervical cultures on Thayer-Martin medium wherein oxidase-positive colonies of gram-negative diplococci appear. In the above culture tests, all cultures are incubated for 18 hours at 37° C. with $CO_2$ enrichment. The cultural results are frequently confirmed by sugar fermentation studies.

Other tests employed include complement fixation wherein the hemolysis of erythrocytes is monitored. This test is time consuming, the accuracy of results is questionable, and standardization of reagents is a problem. Indirect immuno fluorescence is also employed to measure the amount of gonococcal antibody in sera. However, this test requires complex and costly apparatus as well as a skilled operator.

Experimental progress was made in 1963 when Kellog et al. (J. Bacteriol., Vol. 85, pages 1274–1279) identified four clonal types of *N. gonorrhoeae* bacteria and demonstrated a correlation between colonial morphology and virulence with two of the four colonial types. The four types are designated as $T_1$, $T_2$, $T_3$, and $T_4$, with the clonal type one (i.e., $T_1$) being identified as the primary virulent strain most likely to reflect the antigenic stimulation responsible for antibody production in humans. It is also known that a particular strain of N. gonorrhea designated as F62 will undergo immunochemical region with antibodies developed in response to a wide variety of other strains of N. gonorrhea. Based on this work, a number of different antigens have been derived from the F62-$T_1$ strain. Examples of this approach are: Lee et al (Infec. Immun., Vol. 1, pages 207–208); Schmale et al. (J. Bacteriol., Vol. 99, pages 469–471); Reising et al (Appl. Microbiol., Vol. 18, pages 337–339); and Lee at al (Appl. Microbiol., Vol. 21, pages 852–853).

While much effort has been expended to develop suitable gonorrheal antigens, there still exists a need to apply previous work in a practical manner to produce an immunochemical test for gonorrhea. Specifically, a need exits to find a carrier particle which can be sensitized with a gonorrheal antigen so that the immunochemical reaction with gonorrheal antibodies can be followed visually to ascertain the presence of infection.

Schuurs (U.S. Pat. No. 3,551,555) teaches that various types of carrier particles (e.g., synthetic latexes or cholesterol crystals) can be presensitized with an inert protein and subsequently sensitized with various materials such as antigens of bacterial origin. It is also known (Reising, Appl. Microbiol., Vol. 21, pages 852–853) that cholesterol particles can be presensitized with lecithin and sensitized with gonorrheal antigen derived as an aqueous supernatant by disruption of cells of gonorrhea bacteria. However, by the resulting test, a microflocculation assay, in females diagnosed clinically and culturally to have gonorrheal infection, only 76% showed a positive microflocculation assay. In males, the correlation was only about 50%. Therefore, while immunochemical testing using some form of presensitization of carrier particles is known, the results as evidenced by the above assay technique have not been sufficiently sensitive to be used in place of the present culture techniques, or on a mass screening basis.

DESCRIPTION OF THE INVENTION

The invention is a reagent for the detection of gonorrheal antibodies in human blood serum or synovial fluid by the immunochemical reaction of the antibodies with the reagent. The essential reactive component of the reagent is a supply of spheroidally-shaped latex particles having an average particle diameter of from 0.2 to 1.3 microns. The particles have absorbed upon their surface both a presensitizing protein which is inert to the immunochemical reaction and is also a simple protein in that it liberates alpha amino acids upon hydrolysis. Also absorbed upon the particles is a heat labile gonorrheal antigen derived from Neisseria gonorrhoeae bacteria exhibiting $T_1$ colonial morphology.

In testing, the reagent of the invention is admixed with human blood serum or synovial fluid obtained from the patient under study. If gonorrheal antibodies are present in the serum, this will be evidenced by agglutination upon admixing the serum with the latex reagent. If the test serum is free of gonorrheal antibodies, there is no reaction and agglutination does not take place. Where the carrier particles are present in the form of a dried deposit, a liquid should be used to reconstitute the particles into a liquid suspension prior to admixture with the serum.

The advantages of the invention as described above are significant in view of the present widespread incidence of gonorrheal infection. The test employing the agent of the invention requires only a few minutes for its completion and can be performed "on the spot". These advantages are especially significant when contrasted with the widely used culture methods where a specimen is taken at one location and must be shipped to another location, usually a laboratory, for the organisms to be cultured. The customary culture test may take as long as two weeks before results are obtained. Culture results can also be erroneous, especially in women, if only one site is cultured or if rather exacting conditions for preservation, shipment, and culturing of the bacteria are not followed.

Most significantly, the test results obtained are accurate in detecting the presence of gonorrheal antibody in groups such as women and patients suffering from gonorrheal arthritis and other forms of complicated gonorrhea, where diagnosis is often time consuming and inconvenient. There is a high probability that infection will be detected where it is present in women and cases of complicated gonorrhea. These results are very helpful in that gonorrheal infection is usually difficult to detect in women because a large percentage (e.g., 80%) do not exhibit symptoms and must frequently be cultured at more than one site to detect infection. Cases of gonorrheal arthritis frequently do not give a positive culture test. For these reasons, the present invention is ideally suited for use as a routine screening device in hospitals and prenatal clinics. As a good example, in cases of pelvic inflammatory disease in women, the present invention can be used to detect or rule out gonorrheal infection. Using the invention, many cases of infection can be detected and can be subsequently confirmed by other, more expensive and time consuming means if this is thought to be desirable.

PREPARATION OF LATEX REAGENT

The synthetic particles of the invention are prepared according to the following general procedure. The particles are received from the manufacturer in the form of a suspension and are sedimented by centrifugation, whereupon they are resuspended in a solution of the inert protein, preferably in a buffer, where absorption of the protein onto the particles takes place. Next, the excess of inert protein is removed, for example, by centrifugation of the particles. Subsequently, absorption of the gonorrheal antigen is brought about by suspension of the particles in an aqueous solution of the antigen. This step is referred to as sensitization.

In the presensitization step, it is thought that the inert protein acts to coat a certain number of the "sites" on the particle to which foreign materials such as the protein or antigen can be attached. The number of sites is believed to vary with the size and composition of the latex particle. Because the inert protein is employed in definite predetermined amounts, a number of reactive sites on the carrier particle are blocked and are unavailable to the antigen. In this manner, an over abundance of antigen on the particle is avoided. Also, the latex particles exhibit an affinity for one another and even after coating with antigen, the particles tend to clump together. This tendency interferes with the sensitivity of the agglutination reaction by coating with inert protein, the affinity of the particles for themselves is lessened, i.e., the inert protein is believed to be a very effective dispersing agent and contributes significantly to the improved sensitivity of the present invention although it is the combination of three components, inert protein, latex, and specific antigenic material which is most significant.

If the coating of inert protein is too great, much of the particle surface is thought to be precluded from absorbing the gonorrheal antigen. This results in a latex reagent which is not sufficiently sensitive to detect antibodies present in relatively small amounts, i.e., because of the over abundance of presensitizing protein, the antigen sensitization reaction may not be successful. The temperature at which the latex particle is sensitized and the time of exposure of the particle to the antigen solution are also known to be factors. The temperature is thought to be important because the antigen employed in the invention is heat labile, i.e., it tends to lose its tendency to agglutinate gonorrheal antibodies if exposed to temperatures above a certain point, i.e., 55° C.

From the above discussion, it can be seen that production of the latex reagent is dependent upon successful coordination of a number of variables, i.e., size of latex particles, latex concentration in both the presensitizing and sensitizing steps, the concentration of inert protein, the antigen concentration, and the temperature at which the sensitization reaction is carried out as well as the time of exposure of the latex particles to the antigen solution.

To optimize the variables involved, a checker-board type of routine should be followed, i.e., the variables are matched at different levels, one against the other. Successful optimization is determined by challenging the sensitized latex reagent against a panel of sera selected from low risk groups, i.e., healthy children, celibate adults, and individuals proven not to be infected with *N. gonorrhoeae* by reason of repeated negative coltures. A highly selective reagent with good sensitivity should yield no false-positive reactions. Another panel of sera from individuals known to have gonorrhea by reason of positive culture results is also tested against the reagents. At least 95% should yield positive test results.

For polystyrene latexes, the above variables are generally controlled as follows. In carrying out the presensitization reaction, the pH of the suspension is maintained within the range of from 7 to 9, the concentration of latex particles is from 1.5 to 3% by weight of the suspension, and the amount of inert protein employed is from 0.15 to 1.2 milligrams per milliliter of the suspension. In the sensitizing step, the pH and particle concentrations correspond to those of the presensitizing step and the amount of antigen employed is within the range of from 0.0625 to 0.5 milligrams per ml. of suspension. In the sensitization step, an optimum temperature is about 37° C. with about one-half hour being an optimum time for exposure of the latex to the sensitizing solution of antigen.

As used herein, the term "inert protein" refers to a protein which does not participate in the immunochemical reaction and does not influence the gonorrheal antibodies detrimentally. It is understood, however, that such a protein must have an affinity for the resin particle. Suitable inert proteins include conjugated or nonconjugated proteins, the peptides of varying molecular weights and proteins of vegetable origin. Good results are generally obtained by using a simple protein in that this class of proteins is least likely to react detrimentally in the immunochemcial reaction or with the antigen coating applied to the carrier particle. By the term "simple protein" it is meant proteins yielding primarily α-amino acids or their derivatives when subjected to hydrolysis. This group includes albumins (e.g., serum albumin and egg albumin), globulins (e.g., hemoglobin and lactoglobulin), alcohol soluble proteins, histones (e.g., globin in hemoglobin), and protamines (e.g., sturine and salmin).

The synthetic resin suitable for absorbing the antigen must be capable of absorbing protein and must be capable of being prepared in spherical or near spherical shape having an average diameter of from about 0.2 to about 1.31 micron. The term "spheroidal" is used sometimes to indicate the shape of spherical and near-spherical particles. Examples of suitable synthetic resins are polystyrene and acrylic latexes. Preferably, a polystyrene latex is employed having an average particle diameter of about 0.50 micron. As set forth above, following sensitization, the concentration of particles in the suspension should be from about 1.5 to 3% by weight of the suspension. If the concentration of particles in the suspension is less than about 1.5% by weight, agglutination of the particles does not readily occur; and when it does occur, it is not readily observed. If the concentration of particles in the suspension is above about 3% by weight, the number of particles is too great to allow an accurate determination of whether or not agglutination occurred.

PREPARATION OF GONORRHEAL ANTIGEN

In preparing gonorrheal antigen for use in the invention, it is critical that a properly virulent strain of the bacteria be employed. Work by Kellogg et al (J. Bacteriol., Vol. 85, pages 1274–1279) has demonstrated that four clonal types (and perhaps five) of *Neisseria gonorrhoeae* exist and these have been designated respectively as $T_1$, $T_2$, $T_3$, and $T_4$. However, virulence is thought to be associated primarily with the $T_1$ clonal form, and perhaps to some extent with the $T_2$ form. In culture studies, it has been observed that $T_1$ colonies tend to develop or mature into $T_2$ colonies. Therefore, while $T_1$ conlonies most likely reflect the antigenic stimulation responsible for antibody product in humans, $T_2$ forms may also be antigenic. In preparing the gonorrheal antigen employed in the invention, use is made to $T_1$ colonies, but it is understood that $T_2$ colonies may also be present although preferably the $T_2$ colonies will be present only to a minor extent, e.g., less than 20% of the total colonies. Suitable $T_1$ colonies may be prepared by use of a suitable culture medium accompanied by selective transfers in vitro of $T_1$ colonies. This procedure is described by Kellogg et al in the journal article previously referred to.

In practicing the invention, the $T_1$ clonal form of the Gc9 strain of *N. gonorrhoeae* has been found to yield a very good antigen which will undergo immunochemical agglutination with antibodies produced by a large number of other strains of the gonococcus. However, as will be realized, evolution of the gonococcus may yield strains whose antibodies agglutinate poorly, if at all, with Gc9 antigens. Also, new types of gonococcus bacteria may be discovered. In this event, in practicing the invention, the gonorrheal antigen should be obtained from the $T_1$ clonal forms of whatever strain is involved. $T_1$ colonies are characterized by their glistening convexity, dark brown to black coloration, and small size (0.5 mm. to 0.9 mm.). These characteristics are noted by observance of growth on a transparent medium with the use of diffuse angled light transmitted through the medium from below the plate. With defferent strains, the colony size may fall outside the above range, but the glistening convexity and dark coloration remain. $T_1$ colonies and methods of culturing are further described by Kellogg et al, J. of Bacteriol., Vol. 96, pages 596–605. This article also contains a number of references also describing $T_1$ colonies (and also $T_2$ colonies).

While much work has been carried out using the Gc9 strain, any antigenic strain of *Nisseria gonorrhoeae* can be employed. For example, the following work has been carried out:

I. Sensitization of latex with an antigen derived from and identified as a wild strain (K.) obtained from the New Jersey College of Medicine and Denistry;

II. Sensitization of latex with an antigen derived from and identified as strain K4A; with an antigen from ATC 23050;

III. Sensitization of latex with antigen derived from and identified as having a smooth (S) or rough (R) morphology from strain 821 obtained from Norfolk V.D. Clinic;

IV. Sensitization of latex with antigen derived from and identified as a wild strain, Gc 01618, from Memphis; and V. Sensitization of latex with antigen derived from and identified as a wild strain, Gc 00102, from Memphis.

In preparing antigen from strains I–V and in sensitizing latex, the same procedures are employed as with Gc9. While latex sensitized with the non-Gc9 strains can be used to detect gonorrheal antibodies, the Gc9 strain has so far proved to be the most sensitive and is preferred for this reason.

An example of a suitable culture medium is a mixture of Gc Medium Base (Difoc) plus Gc Agar Base (Baltimore Biological Laboratories) with 1% of a modified defined supplement composed of cocarboxylase (0.002 g.), glutamine (1.0 g.), dextrose (40.0 g.), and ferric nitrate (50 mg.) dissolved in 100 ml. distilled water and sterilized by filtration (Seitz ED). The plates are incubated under increased carbon dioxide tension (candle extinction) in jars at 35° to 37° C. for 18–24 hours. The cell crop is subsequently harvested in distilled water for preparation of the antigen. In culturing the $T_1$ bacteria, it has been discovered that the Gc Medium Base tends to increase the rate of growth of the bacteria but that the growth tends to contain large portions (e.g., 30%) of other clonal forms. Growth with Gc Agar Base produces a higher percentage of $T_1$ colonies, but is slower than with the Gc Medium Base. Generally, a 1/1 mixture of the two bases is satisfactory, but the ratio can be varied to speed up growth or create more selective growth.

From the harvested cells, the bacterial antigen is obtained by disrupting the $T_1$ bacterial cells to obtain their main morphological elements, i.e., cell walls and protoplasm. The disruption is carried out in an aqueous medium and the cell walls and other insoluble portions are separated by sedimentation with a centrifuge. The supernatant contains the desired antigen. The exact method of disruption is not critical and can be accomplished, for example, by ultrasonic disintegration, grinding with abrasives, freeze-thawing, shaking with glass beads, or high-pressure extrusion. The preferred method involves sonification of an aqueous dispersion of cells at 10 to 15 Khz., for a period of one-half to $1\frac{1}{2}$ hours at a temperature of 2° to 8° C. Thereafter, the cell walls and other insolubles are sedimented by centrifugation and discarded. Again, the temperature is maintained at 2°–8° C. The supernatant is freeze-dried to yield antigenic material used in sensitizing the synthetic resin particles.

Variations of the above procedure for preparing antigen may also be employed. These are exemplified as follows:

a. Freeze-dried antigen is reconstituted with sterile distilled water and subjected to a second sonication for one hour at maximal setting. The material is then centrifuged at high speed and the supernatant drawn off and freeze dried.

b. Cultures harvested in distilled water are sonicated for one hour at maximal setting and the entire sonified material freeze dried without prior differential centrifugation.

c. A phenol extraction of the antigen may be accomplished by heating equal portions, for example, 50 ml. of 90% phenol together with 50 ml. of an aqueous suspension of $T_1$ colony growth at 65°–68° C. for 30 minutes. This is transferred to a separatory funnel and the water and phenol phases allowed to separate at 5° C.

The phenol phase is drawn off and dialyzed against buffered saline, pH 7.2. Composition per liter of the buffer is 0.3530 gm. $NaH_2PO_4$, 0.6390 gm. $Na_2HPO_4$, 0.1720 gm. NaCl. Frequent changes of buffer are necessary and dialysis is continued until the bromine test for phenol is negative. The material is then subjected to freeze-drying.

d. A harvest of *N. gonorrhoeae* is sonicated and freeze-dried. This is then resuspended in a buffer, for example, 0.1M Tris, 1.0M NaCl buffer at pH 8.0, and centrifuged for 30 minutes at 11,800 r.p.m. The supernatant is drawn off and placed on a G-200 lybradrex column, a UV scan started, and samples collected. The resultant amounts are grouped into portions and dialyzed against distilled water. Each portion is then freeze-dried.

e. Organisms are grown in a liquid medium, the bacterial cells separated from the liquid, and the liquid dialyzed against water, then freeze-dried for use.

In testing for the presence of gonorrheal antibodies, it has been discovered that the accuracy of test results can be improved by as much as 5% if an absorbing antigen is employed as an additional testing component. For example, in testing females from a low-risk population (e.g., persons from celibate religious orders), an accuracy level as high as 95% may be obtained by using the absoring antigen in combination with the latex reagent of the invention. In carrying out the test, serum would first be admixed with the absorbing antigen and would subsequently be admixed with the latex reagent. Agglutination indicates the presence of antibodies to *N. gonorrhoeae*.

Absorbing antigens employed include Forssman antigen which may be prepared as follows: Guinea pig tissue rich in Forssman antigen (i.e., kidney, spleen, lung) is blended in sufficient 0.9% sodium chloride solution to make an 18% suspension. This suspension is clarified by centrifugation, incubated for 30 minutes at 56° C., recentrifuged, and made 0.2% with respect to sodium azide. Also employed is beef stroma antigen which may be prepared as described below. Preferably, the absorbing antigen will consist of equal parts by weight of beef stroma antigen and guinea pig antigen.

Blood serum to be tested for gonorrheal antibodies is prepared by centrifuging blood specimens at a force that is sufficient to separate the serum or plasma from the cells. Prior to testing the specimen can be retained in the original collection tube. There is no need to heat the specimen or subject it to further processing prior to testing. The suspension of carrier particles and the solutions of absorbing antigens can be employed in liquid form if desired.

TEST SLIDES

A particularly advantageous embodiment of the invention is a test slide comprising a substantially planar strip of substrate material having at least one surface on which the gonorrheal test can be carried out. The latex reagent of the invention is carried on the test surface in the form of a solid dried deposit. Where an absorbing antigen is employed, the test surface carries two separate deposits of dried reagents, one deposit being the latex reagent and the other deposit being the absorbing antigens. The deposits are generally located in close proximity to each other and may if desired be positioned within a demarcated circumscribed test area.

The substrate material may, for example, be glass, glazed porcelain, or a synthetic material, e.g., a plastic material such as nitro cellulose or methyl methacrylate, or a phenol-formaldehyde resin, the surface of which has been treated so as to make it wettable, for example, by sand blasting or rubbing with an abrasive.

Preferably, the substrate is a thin sheet of cardboard having one or both surfaces coated with a coating of a water-impermeable and water-wettable coating of plasticized nitro cellulose, having a thickness which will maintain the flexibility of the cardboard, e.g., about 0.02 inch. In all cases, the surface of the substrate which carries the test reagent deposits should be water-soluble.

With reference to a test slide employing both the latex reagent and an absorbing antigen, the deposited test reagents or spots advantageously have an average diameter between 5 and 10 mm., and are located in close proximity, in order that both may be admixed after being reconstituted to carry out the test. If desired, the coating of the slide may be pigmented with a dark pigment such as carbon black, in order to provide a background of contrasting color against which the test results may be better observed.

In carrying out the test, the latex-antigen deposit is reconstituted with a measured amount (e.g., about 0.03 ml.) of distilled water and the deposit of absorbing antigen is reconstituted by moistening with 0.05 ml. of blood serum to be tested. The reconstituted reagents are admixed to provide a homogeneous reaction mixture which is rocked in a figure-eight motion for two minutes. At the end of this time, the mixture is observed for agglutination using a bright light source. The presence of gonorrheal antibodies is evidenced by agglutination.

To prepare suitable test slides, an approximate quantity (0.03 ml.) of a reagent is accurately measured onto a test slide. The reagent is then dried in dry air, heated at a temperature of about 45° C.

The manner in which quantities of reagents are applied to the slides or cards is immaterial except that the method must be accurate. For example, a suitable method is to employ a metering pump of suitable type, e.g., a Lambda pump, which is a solenoid-operated piston type pump, made of stainless steel, which will deliver from 0.01 cc. (10 Lambda) to 0.5 cc. per stroke, preferably 0.03 cc. The pressure of the issuing fluid is kept below a level which will cause splashing, for example, one drop per stroke, generally 10 strokes per second or less, depending on the rate of delivery desired.

Where two reagents are applied to the slide, they may be each dispensed as a single accurately measured drop side by side simultaneously. The substrate is then removed to a drier and the drops dried at 20° to 50° C., depending upon the heat resistance of the reagent. An optimal temperature is from 40° to 45° C. The dry slide can be used as such, or packaged in a moisture-proof protective container for storage.

In the preparation of the test slides or cards, the latex reagent (and absorbing antigen where employed) is constituted as a solution or suspension in a volatile liquid medium, advantageously an aqueous medium. Such solutions or suspensions may also contain potentiating or resuspending aids. It has been found, in accordance with the invention that a number of adjuvants contribute to the ease of resuspension of dried reagents and serve to produce a firm bonding of the dried reagent to the test slide surface. These adjuvants include, for example, bovine serum albumin in concentrations up to and including 5% (wt./vol.), 1% being optimal; lactalbumin hydrolysate in concentrations up to and including 5%, 1% being optimal; and gum arabic in concentration of about 0.5%.

It has also been found, in accordance with the invention, that the inclusion of a saccharide, such as sucrose or mannitol in the reagent provides, upon drying, a hard, glaze-like finish to the dried test spot which protects it against abrasion and mechanical damage, thereby aiding in packing and storage. The saccharide also provides a matrix which helps to avoid disintegration of the reagent deposit.

EXAMPLE I

The following example illustrates the preparation of the gonorrheal antigen used in sensitizing latex carrier particles.

A culture of *Neisseria gonorrhoeae* bacteria designated as Gc-9 was obtained from the Venereal Disease Research Laboratory, Communicable Disease Center at Atlanta, Ga. This culture consisted of a stabilized virulent bacteria exhibiting $T_1$ colonial morphology. To prepare sufficient stock cultures for experimental purposes, colonies from the Gc-9 culture were multiplied by growing in a specific culture medium and selectively transferring $T_1$ colonies to insure that the resulting cultures remained essentially identical with the original $T_1$ culture. The culture medium was prepared as follows: One liter of gonococcus (Gc) base medium was prepared by mixing 18.0 grams of Difco brand Gc Medium Base (Dehydrated) and 18.0 grams of Agar Base manufactured by Baltimore Biological Laboratories with sufficient distilled water to form one liter of solution. The agar and starch components in the media were dissolved by heating. Following dissolution, the solution media was autoclaved at 121° C. for 15 minutes. Subsequently, the media was cooled to 50° C. and 10.0 ml. of sterile glutamine supplement and 5.0 ml. of sterile ferric nitrate supplement were added. The compositions of the supplements were as follows:

| Glutamine Supplement | | Iron Nitrate Supplement | |
|---|---|---|---|
| Glucose | 400.0 gm. | Ferric Nitrate | 0.5 gm. |
| L-Glutamine (A Grade)* | 10.0 gm. | Distilled $H_2O$ | 500.0 ml. |
| Cocarboxylase | 0.02 gm. | | |
| Distilled Water | 1000.0 ml. | | |

*Calbiochem Corp., La Jolla, California, Grade A material is believed to be free of ammonia and glutamic acid.

Prior to use, the supplements were sterilized by passing through a Seitz or millipore filter and were stored at −20° C. in sterile containers, if not added to the Gc media immediately after preparation.

Following addition of the supplements, the media was mixed well and poured into petri dishes at the rate of 12–15 ml. per plate. Following solidification, the plates were incubated overnight at 37° C. (for drying) and were stored under refrigeration.

Bacteria from the Atlanta Gc-9 culture (or other $T_1$ cultures derived therefrom by selective transfer of $T_1$ colonies) were suspended in Tryticase soy broth at the rate of approximately 15 colonies per ml. of broth. A drop of the suspension was spread over the surface of each of the media plates prepared as described above using a glass spreader. The plates were then incubated after candle extinction for 18 to 24 hours in a tightly closed container at 35° C. After incubation, the plates were harvested by scraping the mucoid material into a beaker containing 50–80 ml. of sterile distilled water. Subsequently, sufficient distilled $H_2O$ was added to bring the volume to 300 ml. Gonorrheal antigen was prepared by subjecting the 300 ml. solution to sonication at approximately 20 Khz for 60 minutes at a temperature of 2° to 8° C. This procedure ruptured the cell membranes. The mixture was then centrifuged at 13,500 r.p.m. for 60 minutes at a temperature of 2° to 8° C. The supernatant was poured off and 35 ml. quantities were placed in large flat-surfaced bottles having a large mouth over which was placed a porous cap. The bottles were placed in a freeze while the shelves of a freeze-dried (Virtis lyophilizing chamber) were cooled to −40° C. Transfer of the bottles was made and the vacuum pump started. When the vacuum reached less than 50 microns of mercury, shelf refrigeration was turned off. The material was processed overnight, and the shelf heat turned on the following morning to facilitate final drying of the product. The vacuum was released, the antigen was removed and weighed, and was placed in a dry container. This powdered antigen was employed to sensitize latex as discussed below.

EXAMPLE II

Preparation of Sensitized Latex

A suspension of polystyrene resin particles to be used as carriers for the gonorrheal antigen was prepared as follows: 240 ml. of Dow brand polystyrene latex (30% solids, 0.48 micron particle size) was diluted with distilled water to 5400 ml. After mixing and centrifuging at 8000 r.p.m. for 30 minutes, the supernatant was discarded. The latex was resuspended in 2700 ml. of borate buffer. The borate buffer solution was prepared as follows: To prepare 50 liters of buffer, boric acid (433.5 gm.) and sodium chloride (100.0 gm.) were dissolved in 48 liters of distilled water. The pH was adjusted to 8.2 by addition of 5 normal sodium hydroxide, and a quantity of distilled water was added to form 50 liters of buffer solution. To 2700 ml. of borate buffer was added 1.62 gm. of bovine serum albumin. The albumin was allowed to become wetted and dissolved in the buffer. This 2700 ml. albumin solution was then added to the 2700 ml. of latex-borate solution while constantly swirling the latex.

The suspension was covered and incubated at about 20° to 25° C. (i.e., room temperature) for 90 minutes, mixing every 15 minutes. After centrifuging for 20 mintues, at 8000 r.p.m., the supernatant was discarded and the suspension was reconstituted to 10,800 ml. by addition of borate buffer. Centrifugation was repeated and the suspension was reconstituted to 2700 ml. by addition of borate buffer.

The presensitized latex was sensitized by admixing therewith 2.7 gm. of *N. gonorrhea* antigen (prepared as in Example I) dissolved in 2700 ml. of the borate buffer. The 5400 ml. of sensitized latex was divided into 500 ml. aliquots and maintained at 37° C. for 30 minutes. The material was then centrifuged for 20 minutes, the supernatant was discarded, and the material was reconstituted with 10,800 ml. of borate buffer. This washing procedure was repeated to insure that no antigen material remained which was unattached to the latex. Following the final wash, the suspension was reconstituted to 3600 ml. by addition of a "final suspension fluid" which consisted of 1800 ml. of borate buffer, 216.0 gm. of sucrose, and 1.44 gm. of Rhodamine B. Distilled water was used to bring the suspension volume to 3600 ml. The Rhodamine dye aids in visualization of agglutination and the sucrose provides a matrix for the reagents when processed to form dried deposits as described below. Neither reagent increases the sensitivity of the latex reagent or is necessary in testing for gonorrheal antibodies. For example, when the reagents of the invention are employed in liquid form rather than as dried deposits, the sucrose in not necessary.

EXAMPLE III

Preparation of Absorbing Antigen

Where employed, the absorbing antigen was a mixture of guinea pig and beef stroma antigens prepared according to the following procedure: Guinea pig antigen was prepared by placing a quantity of tissue of the kidney, lung, or spleen, from freshly sacrificed animals into a blender. When the tissue was finely ground and pooled, it was diluted with 0.9% saline to make an 18% (weight/volume) suspension. The suspension was allowed to stand at 2°-8° C. for two hours with occasional mixing. Subsequently, the suspension was centrifuged for 20 minutes at 4500 r.p.m. The supernatant was separated and heated rapidly to 56° C. in a water bath and maintained at this temperature for 30 minutes. Following heating, the material was stored at 2°-8° 'C. for about 24 hours. After 24 hours in the refrigerator, the material was centrifuged at 8000 r.p.m. to clarify and the clear supernatant was poured into a clean storage vessel for further use. Any precipitate was discarded.

BEEF ANTIGEN

Two gallons beef blood were collected in a 7.6% citrate solution at a slaughterhouse and immediately filtered through cotton gauze into an excess of Alsever's pH 6.1 solution. The resulting suspension was held under refrigeration for 7-10 days. The blood was then centrifuged and washed once in 0.9% sodium chloride solution. After centrifugation of the saline-cell mixture, the blood cells were resuspended in borate buffer (pH 7.0) and incubated at 37° C. until stroma developed. This can be determined by removing a sample and centrifuging it at 8000 r.p.m. and examining the resultant layers that have precipitated. When a light brown flocculent layer is abundant, the material should be further processed by centrifuging at 8000 r.p.m. The supernatant was discarded and the resultant precipitate washed in 0.9% sodium chloride solution until the supernatant wash was light straw colored. At every centrifugation any dark tarry material remaining in the centrifuge bottles after resuspension of the lighter flocculent material was discarded. The final light colored precipitate was brought to a volume of 8 liters in a borate buffer (pH 7.0) that contained no sodium chloride.

Absorption Antigen

Equal volumes of the guinea pig antigen and beef stroma antigen were mixed together and dilution of this material made in borate buffer pH 7.0, e.g., one part guinea pig antigen plus one part beef antigen plus two parts borate buffer.

For use as dried deposits, the resultant absorbing antigen contained 6% sucrose as a matrix and an .03 ml. quantity (prior to drying) was used on each test slide.

EXAMPLE IV

Preparation of Test Slides

To form a convenient test kit for detection of gonorrheal antibodies, test reagents prepared as in Examples II and III were placed in separate portions on the surface of a black plastic-coated slide, and were dried to form two "dots" of reagents, one dot containing the latex reagent and the other dot containing the absorbing antigen. Before drying the latex dot contained 0.03 ml. of reagent and the dot absorbing antigen contained 0.03 ml. of reagent. The procedure for applying and drying the reagents to form deposits on the test card surface was essentially as described above. This procedure is also essentially described in U.S. Pat. No. 3,666,421, to Price.

EXAMPLE V

Test Procedure

A sample of human blood serum was obtained from an unknown female donor. By cultural methods, the donor was known to be infected with gonorrhea. The serum was tested using a slide such as in Example IV. In carrying out the test, about 0.05 ml. of serum was allowed to fall from a dropper onto the dot of absorbing antigen and was thoroughly admixed therewith to combine any heterophile antibodies in the serum with the absorbing antigen and prevent interference with the test reaction.

The dot sensitized latex reagent was reconstituted by addition of about 0.03 ml. of distilled water in droplet form. The water was throughly mixed with the latex. The reconstituted latex was then admixed with the mixture of serum and absorbing antigen. Subsequently, the test slide was rocked gently in a figure-eight motion for two minutes. At the end of this time, the slide was examined for agglutination using a bright light source.

It was observed that the test reagents had undergone gross agglutination which is a positive indication of the presence of gonorrheal antibodies in the serum tested, i.e., illumination with a bright light source revealed the formation of visible aggregates of a regular and individual character.

In carrying out the test of the invention, the extent of agglutination in positive cases was generally plentiful and easily observable using a bright light source. In a few instances, however, only slight agglutination was observed, but this also was taken as a positive reaction indicating the presence of gonorrheal antibodies.

EXAMPLE VI

A control group of patients was tested in accordance with the test procedure of the present invention as exemplified in Example V. The total number of sera tested were 1,441. In the control, sera was present from the following types of sub-groups: a culture negative population (male and female) presumed not to have gonorrheal infection; female celibate population presumed not to have gonorrheal infection; positive males as determined by urethral cultures; positive females as determined by cervical cultures; persons having gonococcal arthritis; men receiving meningitis vaccine; children recently vaccinated (e.g., for diphtheria, typhoid, and tetanus (DPT) or live attenuated measles vaccine); and healthy children.

The testing results achieved on the above control groups are set fourth in Table I.

TABLE I

| Type of Donor | Number of Sera Tested | Test Results Positive | Negative |
|---|---|---|---|
| High and Low risk population (one negative culture) male and female | 236 | 19 (8%) | 217 (92.0%) |
| Celibate female | 184 | 7 (3.8%) | 177 (96.2%) |
| Positive male | 316 | 243 (76.9%) | 73 (23.1%) |
| Positive female | 475 | 442 (93.1%) | 33 (6.9%) |
| Gonococcal arthritis | 54 | 53 (98.1%) | 1 (1.9%) |
| Receiving meningitis vaccine | 21 | 4* | 17 |
| Children receiving vaccines | 55 | 9** | 46 |
| Children | 100 | 2 (2%) | 98 (98%) |

*No culture, sexually active adult males
**Live attenuated measles vaccine (post inoculation)

From the data in Table I, it will be noted that a small number of false positive reactions were obtained in several of the different types of donors tested.

In testing for gonococcal arthritis, there is almost a 100% correlation between test results nad the clinical diagnosis.

In children, the DPT group did not exhibit false positives. However, several false positive reactions were observed in children having received live attenuated measles vaccine. Upon following these donors, the false positives proved to be transient and dropped off the negative after two to three weeks, again presumably due to a decrease in a non-specific antibody titer.

In males testing culturally positive, there was some incidence of false negative reactions, especially in the first week after the infection was contracted. This is believed to be due to several factors. Because of the painful nature of the gonorrheal infection in males, there is a tendency to become aware quickly of the disease and seek treatment. Therefore, while culturally positive results may be obtained, once treatment has begun, the antibody titer is believed to be minimal if at all present, so that serologically the individual gives a negative reaction. Also, it is possible that because of the localized nature of the infection in males, antibody titers are slow to rise to the level where they are detectable by serological methods, especially if treatment has begun. Therefore, in the first week following contraction of the infection, some false negative reactions may arise.

In testing according to the invention, it is advisable to obtain some indication of the prior medical history of the patient, particularly with regard to meningitis infections, some indication should be obtained as to the possible exposure to gonorrheal infection.

EXAMPLE VII

This example illustrates the use in liquid form of the reagents of the invention.

A sample of human blood serum was obtained from an unknown female donor. By cultural methods, the donor was known to be infected with gonorrhea.

A suspension of latex carrier particles sensitized with gonorrheal antigen was prepared as in Example II, with the exception that sucrose (2%) was not added. The suspension was agitated to insure homogeneous suspension. Onto a test card was placed one free-falling drop of test serum (about 0.05 ml.) along with about 0.03 ml. of a glycine buffer (pH 8.2). The buffer and test serum were admixed and one drop (0.03 ml.) of sensitized latex antigen was added and admixed with the buffer and test serum. With a gentle, alternating motion, the test slide was rocked in a figure-eight motion for 2 minutes. At the end of this time, the slide was examined for agglutination using a bright light source. The results were interpreted as described in Example V and the test results were positive.

Other tests were conducted using the above procedure. In a large number of tests, 0.03 ml. of a liquid solution of absorbing antigen was employed in place of the buffer solution. This absorbing antigen was prepared as in Example II.

The results of the tests are set forth in Table II.

TABLE II

| | Glycine Buffer | | | Absorbing Antigen | | |
|---|---|---|---|---|---|---|
| | Total | Pos. | Neg. | Total | Pos. | Neg. |
| General (high and low risk population) | 65 | 15 (23.1%) | 50 (76.9%) | 63 | 7 (11.1%) | 56 (88.9%) |
| Culture Positive Females | 147 | 136 (92.5%) | 11 (7.5%) | 127 | 115 (90.6%) | 12 (9.4%) |
| Culture Positive Males | 98 | 77 (78.6%) | 21 (21.4%) | 97 | 72 (74.2%) | 25 (25.8%) |
| Gon. Arthritis | 23 | 23 (100%) | 0 | 23 | 23 (100%) | 0 |
| Meningococcal carrier | 1 | 0 | 1 | 1 | 0 | 1 |

From Table II it can be seen that the test results in women and in complicated cases of gonorrhea, e.g., gonorrheal arthritis, are very good. There is a high probability that infection will be detected where it is present in these two groups. These results are very helpful in that gonorrheal infection is usually difficult to detect in women because a large percentage of women (e.g., 80%) do not exhibit symptoms and must frequently be cultured at more than one site to detect infection. Cases of gonorrheal arthritis frequently do not give a positive culture test. For these reasons, the present invention is ideally suited for use as a routine screening device. As a prime example, in cases of pelvic inflammatory disease in women, the present invention can be used to detect or rule out gonorrheal infection. Using the invention, many cases of gonorrhea can be detected and can be subsequently confirmed by other, more expensive and time consuming means if this is thought to be desirable.

From Table II, it can be seen that infection in males is not as readily detected as in women. One primary reason for this result is thought to be that a large percentage of men develop symptoms and therefore seek treatment at an earlier stage, before the antibody titer has had time to develop so that infection is not detectable by serological methods. In other studies, in addition to those of Table II, males have consistently tested lower than women. However, it is felt that the need for a detection test for men is not so acute as it is with women and in cases of complicated gonorrheal infection. Also, the present invention should be of use in the smaller percentage of men who are asymptomatic in that these individuals are not likely to seek prompt treatment, thus allowing the antibody titer in the serum to rise to detectable levels. On this basis, the present invention would also be of use for routine screening to detect asymptomatic males in the armed services, for example, or in penal institutions.

What is claimed is:

1. A reagent for the detection of gonorrheal antibodies in human blood serum or synovial fluid by the immunochemical reaction of the antibodies with gonorrheal antigens, consisting essentially of a supply of spheroidally-shaped latex particles having an average diameter of from 0.2 to 1.3 microns, said particles having adsorbed upon their surface
   a. presensitizing protein, which is a dispersing agent for the particles and which is inert to and does not participate in the immunochemical reaction and does not detrimentally influence the antigen and antibody in the reaction, and
   b. a sensitizing soluble heat labile gonorrheal antigen from ruptured bacterial cells of an antigenic strain of Neisseria gonorrhoeae bacteria exhibiting $T_1$ colonial morphology.

2. The reagent of claim 1 wherein the latex is polystyrene latex.

3. The reagent of claim 2 wherein the average diameter of the latex particles is about 0.50 micron.

4. The reagent of claim 1 wherein the inert protein is a serum albumin.

5. The reagent of claim 4 wherein the inert protein is bovine serum albumin.

6. A test slide adapted for the performance on the surface thereof of an immunochemical test for detection of gonorrheal antibodies in human blood serum or synovial fluid, having as essential elements a substantially planar strip of substrate material having at least one test surface whereon is positioned (1) a deposit of solid dried latex particles having a generally spheroidal shape and having an average particle diameter of from 0.2 to 1.3 microns, said particles having adsorbed upon their surface, (a) a presensitizing protein which is a dispersing agent for the particles and which is inert thereto and does not participate in the immunochemical reaction and does not detrimentally influence the antigen and antibody involved in the reaction, and (b) a sensitizing soluble heat labile gonorrheal antigen from ruptured bacterial cells of an antigenic strain of Neisseria gonorrhoeae bacteria exhibiting $T_1$ colonial morphology, (2) a second dried deposit of absorbing antigen capable of combining with heterophile antibodies in said serum or synovial fluid, said test deposits being positioned in close proximity on said test surfaces.

7. The test slide of claim 6 wherein the test surface carries a demarcated test area wherein said dried deposits are situated.

8. The test slide of claim 6 wherein the substrate material is a substantially rectangular sheet of cardboard carrying on one surface a coating of a water-impermeable and water-wettable synthetic material.

9. The test slide of claim 8 wherein the synthetic material is a thin layer of plasticized nitrocellulose.

10. The test slide of claim 6 wherein the deposit of absorbing antigens includes both guinea pig and beef stroma antigens.

11. The test slide of claim 6 wherein the latex is polystyrene latex.

12. The test slide of claim 11 wherein the average diameter of the latex particles is about 0.50 micron.

13. The test slide of claim 6 wherein the inert protein is a serum albumin.

14. The test slide of claim 13 wherein the inert protein is bovine serum albumin.

15. A method for preparing synthetic resin particles presensitized with inert protein and sensitized with gonorrheal antigen, comprising the steps of (a) presensitizing an aqueous suspension of spheroidal latex particles having a diameter of from 0.2 to 1.3 microns with an aqueous solution of inert protein which is a dispersing agent for the particles and which is inert thereto; (b) sensitizing the latex particles by admixing the presensitized latex particles, in the form of an aqueous buffered suspension, with a solution of soluble heat labile gonorrheal antigen from ruptured bacterial cells of an antigenic strain of Neisseria gonorrhoeae bacteria exhibiting $T_1$ colonial morphology made by subjecting the bacterial cells to disruption in an aqueous medium and recovering the aqueous-soluble portions as an aqueous solution, the resulting sensitized particles providing a reagent for detecting gonorrheal antibodies in human blood serum or synovial fluid by immunochemical agglutination.

16. The method of claim 15 wherein the latex is polystyrene latex.

17. The method of claim 16 wherein the average diameter of the latex particles is about 0.50 micron.

18. The method of claim 15 wherein the inert protein is a serum albumin.

19. The method of claim 18 wherein the inert protein is bovine serum albumin.

20. The method for detection of gonorrheal antibodies in human blood serum or synovial fluid by means of the immunochemical reaction of said antibodies with gonorrheal antigens, which comprises (1) admixing a sample of said serum or fluid with an absorbing antigen capable of combining with heterophile antibodies in said serum or synovial fluid, and (2) further admixing with mixture (1) a reagent having as its essential reactive component a supply of spheroidally shaped latex particles having an average diameter of from 0.2 to 1.3 microns, said particles having adsorbed on their surface (a) a presensitizing protein, which is a dispersing agent for the particles and which is inert to and does not participate in said immunochemical reaction and does not detrimentally influence the antigen and antibody involved in the reaction, and (b) a sensitizing soluble heat labile gonorrheal antigen from ruptured bacterial cells of an antigenic strain of Neisseria gonorrhoeae bacteria exhibiting $T_1$ colonial morphology.

* * * * *

UNITED STATES PATENT OFFICE
CERTIFICATE OF CORRECTION

Patent No. 4,066,744      Dated January 3, 1978

Inventor(s) Richard T. Price and Rita C. Prodell

It is certified that error appears in the above-identified patent and that said Letters Patent are hereby corrected as shown below:

In Column 1, line 31, "portions" should be replaced by --positive--.

In column 1, line 60, "region" should be replaced by --reaction--.

In column 2, line 5, "exits" should be replaced by --exists--.

In column 2, line 57, "agent" should be replaced by --reagent--.

In column 3, line 25, --resin-- should be inserted between "synthetic and "particles".

In column 4, line 21, "coltures" should be replaced by --cultures--.

In column 5, line 26, "conlonies" should be replaced by --colonies--.

In column 5, line 27, "product" should be replaced by --production--.

In column 5, line 54, "defferent" should be replaced by --different--.

In column 7, line 34, "absoring" should be replaced by --absorbing--.

In column 8, lines 19-20, "water soluble" should read --water-insoluble--.

In column 10, line 16, "freeze" should be replaced by --freezer--.

In column 10, line 17, "dried" should be replaced by --drier--.

In column 11, line 12, "in" should be replaced by --is--.

In column 14, the Table II should be printed as follows:

UNITED STATES PATENT OFFICE
CERTIFICATE OF CORRECTION

Patent No. 4,066,744          Dated January 3, 1978

Inventor(s) Richard T. Price and Rita C. Prodell

It is certified that error appears in the above-identified patent and that said Letters Patent are hereby corrected as shown below:

TABLE II

|  | Glycine Buffer | | | Absorbing Antigen | | |
|---|---|---|---|---|---|---|
|  | TOTAL | POS. | NEG. | TOTAL | POS. | NEG. |
| General (high and low risk population) | 65 | 15 (23.1%) | 50 (76.9%) | 63 | 7 (11.1%) | 56 (88.9%) |
| Culture Positive Females | 147 | 136 (92.5%) | 11 ( 7.5%) | 127 | 115 (90.6%) | 12 ( 9.4%) |
| Culture Positive Males | 98 | 77 (78.6%) | 21 (21.4%) | 97 | 72 (74.2%) | 25 (25.8%) |
| Gon. Arthritis | 23 | 23 (100%) | 0 | 23 | 23 (100%) | 0 |
| Meningococcal Carrier | 1 | 0 | 1 | 1 | 0 | 1 |

Signed and Sealed this

Sixth Day of June 1978

[SEAL]

Attest:

RUTH C. MASON
Attesting Officer

DONALD W. BANNER
Commissioner of Patents and Trademarks